(12) United States Patent
Hontsu et al.

(10) Patent No.: US 8,277,750 B2
(45) Date of Patent: Oct. 2, 2012

(54) DETECTOR FOR CHEMICAL SENSOR DEVICE AND USE THEREOF

(75) Inventors: Shigeki Hontsu, Hirakata (JP);
Masanobu Kusunoki, Iwade (JP);
Hiroaki Nishikawa, Iwade (JP);
Yoshiya Hashimoto, Osaka (JP); Izumi Yamada, Tokyo (JP)

(73) Assignee: Kinki University, Osaka (JP)

( * ) Notice: Subject to any disclaimer, the term of this patent is extended or adjusted under 35 U.S.C. 154(b) by 470 days.

(21) Appl. No.: 11/661,358

(22) PCT Filed: Aug. 30, 2005

(86) PCT No.: PCT/JP2005/015715
§ 371 (c)(1),
(2), (4) Date: Dec. 18, 2007

(87) PCT Pub. No.: WO2006/025358
PCT Pub. Date: Mar. 9, 2006

(65) Prior Publication Data
US 2008/0202926 A1    Aug. 28, 2008

(30) Foreign Application Priority Data
Aug. 31, 2004   (JP) ................... 2004-253536

(51) Int. Cl.
*G01N 21/75*   (2006.01)
*G01N 31/22*   (2006.01)
*G01N 33/52*   (2006.01)
*C12Q 1/68*    (2006.01)
*G01N 27/26*   (2006.01)

(52) U.S. Cl. ............ 422/400; 422/50; 204/400

(58) Field of Classification Search .......... 204/400; 422/50
See application file for complete search history.

(56) References Cited

U.S. PATENT DOCUMENTS

| | | | |
|---|---|---|---|
| 4,456,902 A * | 6/1984 | Komine et al. | 338/34 |
| 4,855,118 A * | 8/1989 | Ichinose et al. | 423/301 |
| 4,971,739 A * | 11/1990 | Ichinose et al. | 264/616 |
| 5,763,191 A * | 6/1998 | Knoll et al. | 435/7.1 |

(Continued)

FOREIGN PATENT DOCUMENTS

GB    2 293 009    3/1996

(Continued)

OTHER PUBLICATIONS

I. V. Fadeev et al. "Synthesis and Structure of Magnesium-Substituted Hydroxyapatite," Inorganic Materials, vol. 39, No. 9, 2003, p. 947-950.*

(Continued)

*Primary Examiner* — Sam P Siefke
*Assistant Examiner* — Bryan Kilpatrick
(74) *Attorney, Agent, or Firm* — Harness, Dickey & Pierce, P.L.C.

(57) ABSTRACT

Disclosed is a detector for chemical sensor devices, the detector being improved in detection sensitivity. Also disclosed is use of such a detector for chemical sensor devices. Specifically, disclosed is a detector for chemical sensor devices by which a substance to be measured is detected by adsorbing the substance contained in a medium on the surface thereof. The detector includes an adsorption layer containing hydroxyapatite or a substituted apatite obtained by substituting a part of elements in hydroxyapatite on a surface which is used for detecting the substance to be measured. Such a detector is greatly improved in detection sensitivity, and thus able to detect a very small amount of a chemical substance.

10 Claims, 4 Drawing Sheets

U.S. PATENT DOCUMENTS

| | | | |
|---|---|---|---|
| 6,645,644 B1 * | 11/2003 | Schwartz et al. | 428/632 |
| 2006/0199729 A1 * | 9/2006 | Naganuma et al. | 502/228 |

FOREIGN PATENT DOCUMENTS

| | | |
|---|---|---|
| JP | 60-14481 B | 4/1985 |
| JP | 63-193054 | 8/1988 |
| JP | 63-257201 A | 10/1988 |
| JP | 06-287008 | 10/1994 |
| JP | 7-128269 | 5/1995 |
| JP | 08-075747 | 3/1996 |
| JP | 2001-153777 | 6/2001 |
| JP | 2003-253424 A | 9/2003 |
| JP | 2003-322653 A | 11/2003 |
| JP | 2004-163259 | 6/2004 |
| JP | 2005-283550 A | 10/2005 |

OTHER PUBLICATIONS

Nakamura et al., "QCM" Preprints of 11$^{th}$ Fall Meeting of the Ceramic Society of Japan, Oct. 1, 1998, ISBN:4-931298-23-0 C3058.

S. Nakamura et al. "Bio-Organic Material Adsorption onto Apatite Films investigated with QCM techniques," Preprints of 11$^{th}$ Fall Meeting of the Ceramic Society of Japan, Oct. 1, 1998, pp. 144.

M. Kusunoki et al. "Quartz Crystal Microbalance Sensor with Hydroxyapatite-coating," Extended Abstract of the 65$^{th}$ meeting of the Japan Society of Applied Physics and Related Societies, Sep. 1, 2004, pp. 1144.

M. Kusunoki et al. "Development of QCM Sensor with Hydroxyapatite Adsorption Layer," Abstract of 2004 Symposium of Japanese Society for Biomaterial, Nov. 15, 2004, pp. 166.

* cited by examiner

F I G. 7 (a)
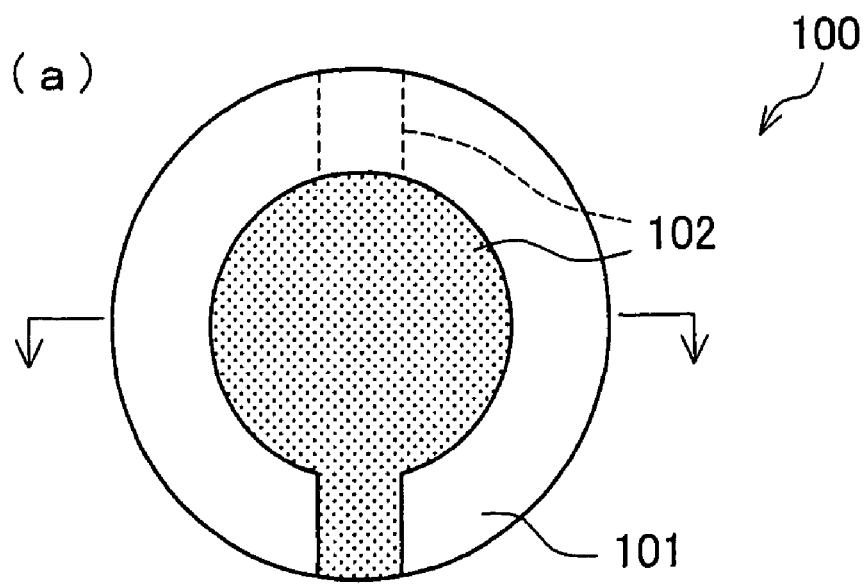
F I G. 7 (b)
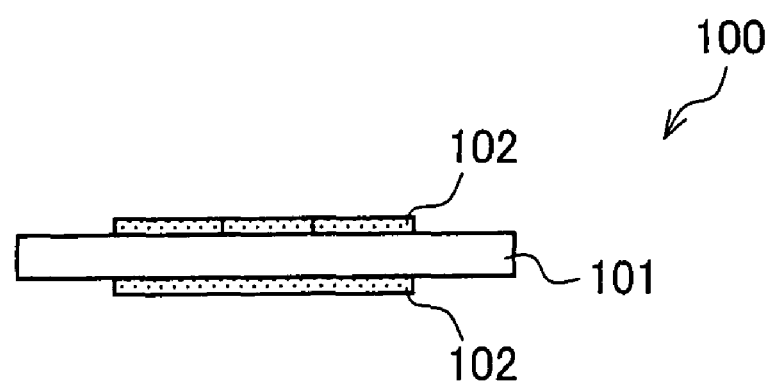

DETECTOR FOR CHEMICAL SENSOR DEVICE AND USE THEREOF

TECHNICAL FIELD

The present invention relates to a detector for use in a chemical sensor apparatus, the detector detecting a chemical substance or biomolecule in a minute quantity, and to use thereof. Especially to the present invention relates to a detector for use in a chemical sensor apparatus, the detector being improved in adsorption efficiency for a chemical substance or the like by utilizing hydroxyapatite and its derivatives.

BACKGROUND ART

Recently, techniques for detecting chemical substances in minute quantities have been developed to detect chemical substances of minute quantities in liquids or gases, or to detect interaction between particulates contained in medium with high sensitivities. Known as such techniques for detecting chemical substances in minute quantities are, for example, Quartz Crystal Microbalance (hereinafter, just referred to as "QCM method") and Surface Plasmon Resonance (hereinafter, just referred to as "SPR method").

The QCM method, in which utilizing microbalance law is applied, is an art for detecting chemical substances or biosubstance by using a quarts crystal oscillator. The QCM method performs quantitative analysis by exposing surfaces of working electrodes of the crystal quartz oscillator to a sample gas or sample solution, and detecting adsorption and desorption of components of the sample to or from the surfaces of the working electrodes by monitoring a change in oscillation frequency of the quarts crystal oscillator.

More specifically, an crystal quartz oscillator 100 includes a thin crystal plate 101, and metal electrodes 102 vapor-deposited on a surface and a reverse surface of the thin crystal plate 101, as illustrated in FIG. 7. When a chemical substance or biomolecule attaches to the metal electrode 102, oscillation frequency is changed proportionally with a weight of a chemical substance or biomolecule attached thereto. That is, when a film of a sample component is formed on the surface of the metal electrode 102 of the quartz crystal oscillator 100 or a substance is adsorbed on the surface of the metal electrode 102 of the quartz crystal oscillator 100, the frequency is shifted according to how much the substance is present on the surface of the metal electrode 102 by weight per unit surface. The frequency shift phenomenon can be an indictor for detecting a chemical substance or biomolecule in a minute quantity in a medium.

A chemical sensor using the QCM method promises stable detection sensitivity because the frequency of the quartz crystal is stable over a wide temperature range. If conditions permit, such a chemical sensor can perform real-time detection of adsorbed substance in 1 to 10 ng (see Patent Citation 1, for example).

Meanwhile, the SPR method is a technique for optically detecting a chemical substance in a minute quantity. More specifically, the SPR method irradiates light on a metal thin film and monitors reflection light therefrom. When a chemical substance attaches on the metal thin film, refractive index of the metal thin film is changed. The SPR method monitors this change thereby to detect the chemical substance in a minute quantity. Chemical sensors using the SPR method have been used in the field of biotechnology, environment, and industry, in order to analyze interactions between biomolecules immobilized on the surface, to monitor antigen-antibody reactions, and to monitor sugar content, for example (see Patent Citation 2, for example).

[Patent Citation 1]
Japanese Patent Application Publication, Tokukai, No. 2001-153777 (published on Jun. 8, 2001)
[Patent Citation 2]
Japanese Patent Application Publication, Tokukai, No. 2004-163259 (published on Jun. 10, 2004)

DISCLOSURE OF INVENTION

The chemical sensor apparatuses using the QCM method or SPR method utilize adsorption of the chemical substance to the detector surface of the electrode, metal thin film, or the like of the quartz crystal oscillator. Therefore, the detection sensitivities of the chemical sensor apparatuses using the QCM method or SPR method are dependent on how much adsorption capacities electrode materials or metal thin film materials have for the substance to be adsorbed thereon. Because of this, the conventional chemical sensor apparatuses are limited in detection concentration and detection sensitivity.

Therefore, there has been a demand for a detector improved in detection sensitivity for a chemical sensor apparatus to be able to detect a chemical substance or biomolecules etc. in minute quantities with high sensitivity.

In view of the aforementioned problems, the present invention is accomplished. An object of the present invention is to provide a detector for use in a chemical sensor apparatus, the detector being improved in the detection sensitivity, and the use thereof.

As a result of diligent works to attain the object, the inventors of the present invention found that a detector can be significantly improved in detection sensitivity by coating its surface with hydroxyapatite or element-substituted apatite, part of whose constituent elements is substituted. The present invention is accomplished based on the finding. More specifically, the present invention encompasses the following inventions (1) to (15) as industrially applicable substances.

(1) A detector for use in a chemical sensor apparatus, the detector detecting a measurement-target substance in a medium by detecting adsorption of the measurement-target substance on a detection surface of the detector, the detector comprising: an adsorption layer on the detection surface for detecting the substance, the adsorption layer comprising an element-substituted apatite which is a hydroxyapatite, part of whose elements is substituted.

(2) The detector as set forth in (1), wherein the adsorption layer is provided over the whole detection surface.

(3) The detector as set forth in claim (1), wherein the adsorption layer is provided over plural parts of the detection surface.

(4) The detector as set forth in any one of (1) to (3), wherein: the adsorption layer comprises an element-substituted apatite that is conductive, and
the adsorption layer functions an electrode.

(5) The detector as set forth in (4), wherein the element-substituted apatite that is conductive is an element-substituted apatite, which is a hydroxyapatite, part of whose elements is substituted with Na.

(6) The detector as set forth in any one of (1) to (3), wherein the adsorption layer comprises an element-substituted apatite that is biocompatible.

(7) The detector as set forth in (6), wherein the element-substituted apatite that is biocompatible is an element-substituted apatite, which is a hydroxyapatite, part of whose elements is substituted with Mg.

(8) The detector as set forth in any one of (1) to (7), comprising: a non-adsorption layer on a surface of the adsorption layer, the non-adsorption layer having an opening for allowing the adsorption layer to contact with the substance in the medium.

(9) The detector as set forth in any one of (1) to (8), wherein the adsorption layer further comprises a substance for bonding specifically to the measurement-target substance so that the adsorption layer selectively adsorbs the measurement-target substance.

(10) The detector as set forth in any one of (1) to (9), wherein the adsorption layer is formed by a laser ablation method.

(11) The detector as set forth in any one of (1) to (10), wherein the adsorption layer is improved in crystallinity of the element-substituted apatite by being subjected to heat treatment or sintering treatment during or after formation of the adsorption layer.

(12) A detector for use in a chemical sensor apparatus, the detector detecting a measurement-target substance, which is contained in a medium and adsorbed on a detection surface of the detector, the detector comprising: an adsorption layer on the detection surface for detecting the substance, the adsorption layer comprising hydroxyapatite, the adsorption layer being formed by a laser ablation method.

(13) The detector as set forth in (12), wherein the adsorption layer is improved in crystallinity of hydroxyapatite by being subjected to heat treatment or sintering treatment during or after formation of the adsorption layer.

(14) The detector as set forth in any one of (1) to (13), wherein the chemical sensor apparatus employs a quartz crystal microbalance method or a surface plasmon resonance method.

(15) A chemical sensor apparatus comprising a detector as set forth in any one of (1) to (14).

The detector according to the present invention has the detection surface on which hydroxyapatite or element substituted apatite is present, which is excellent in adsorption property for particles. Thus, the detector according to the present invention is much greater in the detection sensitivity to the measurement-target substance in the medium, compared with a conventional detector for chemical sensor apparatus. Therefore, the detector according to the present invention makes it possible to detect the measurement-target substance in the medium or interactions between the measurement-target substances with high detection sensitivity. That is, the detector according to the present invention makes it possible to detect chemical substances in lower concentrations.

Furthermore, the use of the detector according to the present invention can provide a chemical sensor apparatus improved in detection sensitivity.

For a fuller understanding of the nature and advantages of the invention, reference should be made to the ensuing detailed description taken in conjunction with the accompanying drawings.

BRIEF DESCRIPTION OF DRAWINGS

FIG. 7(a) is a top view illustrating a structure of a conventional detector for use in an QCM chemical sensor apparatus, viewed from above.

FIG. 7(b) is a cross sectional view of the detector illustrated in FIG. 7(a).

BEST MODE FOR CARRYING OUT THE INVENTION

Figure 1:
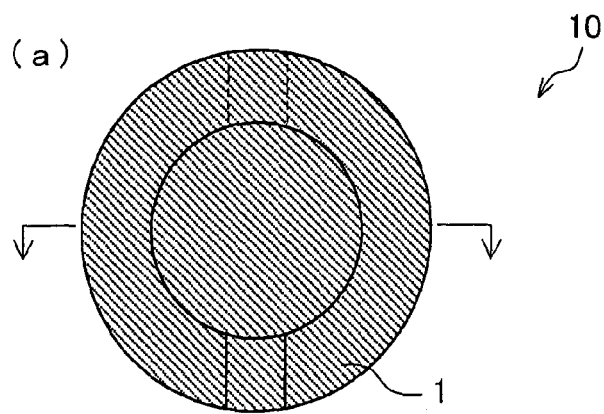
FIG. 1(a) is a top view illustrating a structure of a detector according to one embodiment, viewed from above.
FIG. 1(b) is a cross sectional view of the detector illustrated in FIG. 1(a).
Figure 1:
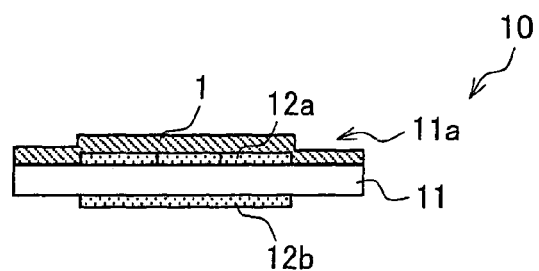

The present invention relates to a detector applicable to chemical sensor apparatus using the QCM method or the SPR method, and the use of the detector. Thus, the following embodiment describe the detector of the present invention first, and then the use of the detector.

<1. Detector According to the Present Invention>

The detector according to the present invention is a detector for use in a chemical sensor apparatus in which a substance in a medium is detected when the substance to be measured (measurement-target substance) is adsorbed on a detection surface. The detector should have an adsorption layer containing hydroxyapatite or element-substituted apatite in which the element is partly substituted. The detector according to the present invention is not particularly limited in terms of its specific configuration (thickness, material made from, dimension, shape).

A theme of the present invention is to improve the detector for the chemical sensor apparatus in detection sensitivity. To achieve this, the adsorption layer containing hydroxyapatite or the like excellent in adsorption capacity of the measurement-target substance is provided on the detection surface on which the detector is to be in contact with the measurement-target substance. Thus, the theme of the present invention is not present in the individual structural characteristics, production methods, etc. specifically described below. Thus, it should be noted that arrangements other than the structures and methods described in each embodiment described below in this DESCRIPTION are also included in the scope of the present invention.

What is meant by the term "medium" in this DESCRIPTION is any medium such as liquid, gas, and the like that allows detection of a substance therein by using a conventionally known chemical sensor apparatus. The medium is not limited particularly in terms of kinds or the like. For example, the medium may be water from a river or sea, air, and the like, or as described in Examples later, various buffers in which biomolecules can be stably kept.

Moreover, the "measurement-target substance" is not particularly limited to a specific arrangement, provided that the substance can be detected when it is adsorbed on the surface of the detector. For example, the chemical substance in particulate forms, ligands, nucleic acids (DNA, RNA, etc.), proteins, peptides, antibodies, signal transduction substance (such as inducing-factors for particular cells, and hormone), and environmental hormone substances, etc.

The "detection surface" is a surface for detecting the measurement-target substance, which is adsorbed thereon. When the measurement-target substance is adsorbed on the detection surface of the detector, characteristics of the detection surface is changed. Thereby, the measurement-target substance is detected. Examples of the detection surface encompass surfaces of the electrodes of the detector (quartz crystal oscillator) for the chemical sensor apparatus using the QCM method, and a surface of the metal thin film of the detector for use in the chemical sensor apparatus using the SPR method.

The "adsorption" encompasses any kinds of physical and chemical adsorption, attachment, bonding, regardless of being specific or non-specific. Further, the "adsorption" encompasses biological and immunological specific bonding.

The "chemical sensor apparatus" can be any chemical sensor apparatus, provided that it can detect a chemical substance in minute quantity contained in the medium. The "chemical sensor apparatus" is not particularly limited to a specific arrangement. But chemical sensor apparatuses chemical sensor apparatuses using QCM method or SPR method are preferable.

What is meant by the term "hydroxyapatite" is not only a substance expressed as $Ca_{10}(PO_4)_6(OH)_2$, but also a water-eliminated mixture of calcium phosphate and hydroxyapatite, the mixture being obtained by heat treatment such as sintering of the hydroxyapatite Moreover, the "element-substituted apatite" can be any hydroxyapatite molecule in which part of the elements is substituted, and is not particularly limited as to kinds and quantities of the elements (substitution element) etc. to be introduced by the substitution. A substitution element for giving higher electric conductivity, and a substitution element for increasing bio-compatibility are especially preferable as the substitution element. The substitution element for giving higher electric conductivity may be, but not limited to, Na, and the substitution element for increasing bio-compatibility may be, but not limited to, Mg. That is, the element-substituted apatite is an apatite that is improved to have a new property as well as the excellent adsorption property of hydroxyapatite.

The "adsorption layer" according to the present invention contains hydroxyapatite or the element-substituted apatite described above. Hydroxyapatite or the element-substituted apatite contains a phosphate group and Ca ions, and excellent in adsorption. The adsorption layer containing such a substance excellent in adsorption is provided on the surface of the detector of the chemical sensor apparatus. This improves the chemical sensor apparatus in detections sensitivity for substances contained in the medium or for interaction between particles, compared with the conventional detector for chemical sensor apparatus.

Moreover, the "adsorption layer" may contain any substance therein, provided that the adsorption layer contains at least hydroxyapatite or the element-substituted apatite. For example, the "adsorption layer" may contain a specifically-linking substance (intermediate substance) that specifically links to the measurement-target substance. This can adjust adsorption strength and bonding strength between the adsorption layer and the measurement-target substance. The specifically-linking substance is preferably a substance that specifically interacts with the measurement-target substance. Examples of the specifically-linking substance encompass ligands, antibodies, inducing-factors for particular cells, and the like substance. By forming such an adsorption layer containing the specifically-linking substance, it is possible to produce a detector that selectively detects the measurement-target substance.

Moreover, the "adsorption layer" can be formed by any way, provided that the adsorption layer is formed on the surface so that the adsorption layer can be in contact with the measurement-target substance. For example, methods conventionally known as coating methods can be employed, such as dipping method, sputtering method, plasma spraying method, laser ablation method, etc. Especially, laser ablation method is preferable. As described in Examples later, the laser ablation method makes it possible to form the adsorption layer in a thin film form. This can improve the surface of the detector without deteriorating the high resolution property that the detector originally has. As a result, the detector can be highly sensitive. For example, the detector on which the adsorption layer is formed may be subjected to heat treatment or sintering treatment at a predetermined temperature in order to attain higher crystallinity, as described in Examples later.

Moreover, the "detector" in the present DESCRIPTION is a device (sensor portion) that is detachably attached to a main body of the chemical sensor apparatus and used to detect the measurement-target substance such as chemical substances etc. in minute quantities. Examples of such a detector encompass a device by which the measurement-target substance is quantitatively measured by detecting its adsorption and desorption by using, as the indicator, the change in the oscillation frequency (in case of the QCM method) or the change in the optical refractive index (in case of SPR method), which change is caused when the measurement-target substance attaches the surface of the detector. More specific examples encompass quartz crystal for use in the chemical sensor apparatus using the QCM method, a device for use in the chemical sensor apparatus using the SPR method, and the like device.

In the following, the detector according to the present invention is explained below in more details referring to the drawing. In the present DESCRIPTION, a device for use in a chemical sensor apparatus using the QCM method is described by way of example. It should be noted that a detector for the chemical sensor using the SPR method may be produced similarly and adopted by a person skilled in the art.

[Embodiment 1]

One embodiment of the present invention is described below referring to FIG. 1(a) and FIG. 1(b). FIG. 1(a) is a top view illustrating a structure of a detector according to one embodiment, viewed from above. FIG. 1(b) is a cross sectional view of the detector illustrated in FIG. 1(a).

As illustrated in FIGS. 1(a) and 1(b), a detector 10 according to the present embodiment includes an adsorption layer 1, a crystal plate 11, and metal electrodes 12a and 12b. The metal electrodes 12a and 12b are provided on either side of the crystal plate 11 such that they face each other with the crystal plate 11 therebetween. The metal electrodes 12a and 12b are smaller than the crystal plate 11 in dimension. That surface of the crystal plate 11 on which the metal electrode 12a is formed is referred to as a surface 11a. The surface 11a is a surface that will contact with a sample (medium) in which the measurement-target substance is contained.

The adsorption layer 1 formed such that the adsorption layer 1 covers the whole surface 11a of the crystal plate 11 on which the metal electrode 12a is formed. That is, the detector 10 has the same arrangement as a conventional detector (such as the detector 100 as illustrated in FIGS. 7(a) and 7(b)), except that the adsorption layer 1 is provided such that the adsorption layer 1 covers that whole surface of the metal electrode which will contact with the measurement-target substance.

In this arrangement, the adsorption layer 1 containing hydroxyapatite or like having excellent adsorption capacity is formed over the whole surface of the surface 11a of the quartz crystal 11, the whole surface includes the metal electrode 12a. This induces adsorption over a wide area thereby to improve the sensitivity as much as possible.

The conventional detector of the chemical sensor apparatus has a limit in detection sensitivity due to low adsorption capacity of the material from which the metal electrode is made. However, the detector 10 with the above arrangement can perform more sensitive detection beyond the limit in detection sensitivity of the conventional detector. That is, the detector 10 can detect a chemical in low concentration, which cannot be detected with the conventional detector.

Moreover, the adsorption layer 1 may contain an element-substituted apatite that is biocompatible. With this arrangement, the detector 10 can be more effective as a means for molecular biological experiments regarding biocompatibility, for example, regarding whether or not the medium contains a inducing-factor of a tissue or the like factor that is more easily adsorbed specifically to the biocompatible element-substituted apatite than the other type of element-substituted apatite or stoichiometric composition apatite.

[Embodiment 2]

One embodiment of the present invention is described below, referring to FIGS. 2(a) and 2(b). Note that the same constituent elements having the same function as the corresponding ones in Embodiment 1 are labeled in the same manner and their explanation is omitted here. That is, only the difference from Embodiment 1 is described here.

Figure 2:
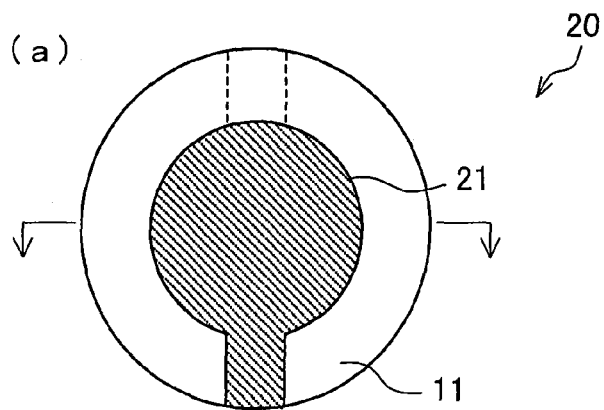
FIG. 2(a) is a top view illustrating a structure of a detector according to one embodiment, viewed from above.
FIG. 2(b) is a cross sectional view of the detector illustrated in FIG. 2(a).
Figure 2:
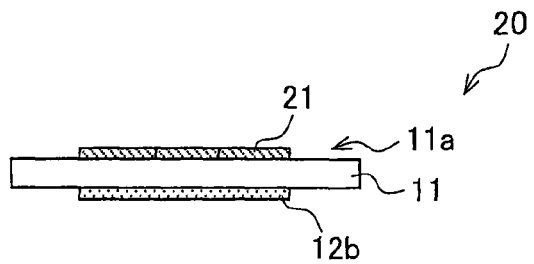

FIG. 2(a) is a top view illustrating a structure of a detector according to one embodiment, viewed from above. FIG. 2(b) is a cross sectional view of the detector illustrated in FIG. 2(a). As illustrated in FIGS. 2(a) and 2(b), a detector 20 according to the present embodiment includes an adsorption layer 21, a crystal plate 11, and a metal electrode 12b. The adsorption layer 21 and the metal electrode 12b are provided on either side of the crystal plate 11 such that they face each other with the crystal plate 11 therebetween. The adsorption layer 21 and the metal electrode 12b are smaller than the crystal plate 11 in dimension. The surface on which the adsorption layer 21 is formed is referred to a surface 11a, which will contact with a sample (medium) containing the measurement-target substance.

The adsorption layer 21 contains an element-substituted apatite that is electrically conductive. So, the adsorption layer 21 itself is electrically conducive. In the present embodiment, the adsorption layer 21 functions as an electrode. That is, the detector 20 has the same arrangement as a conventional detector (such as the detector 100 as illustrated in FIGS. 7(a) and 7(b)), except that the electrically adsorption layer 21 functions as a metal electrode that will contact with the measurement-target substance.

In this arrangement, the adsorption layer 21 containing the electrically conductive element-substituted apatite replaces one electrode (which is usually made of a metallic material) of the detector, and, the adsorption layer 21 also functions as an electrode. This arrangement can make it easier to produce the detector.

In addition, the metal electrode 12b may be an adsorption layer 21 containing an/the element-substituted apatite that is electrically conductive.

[Embodiment 3]

One embodiment of the present invention is described below, referring to FIGS. 3(a) and 3(b). Note that the same constituent elements having the same function as the corresponding ones in Embodiments 1 and 2 are labeled in the same manner and their explanation is omitted here. That is, only the difference from Embodiments 1 and 2 is described here.

Figure 3:
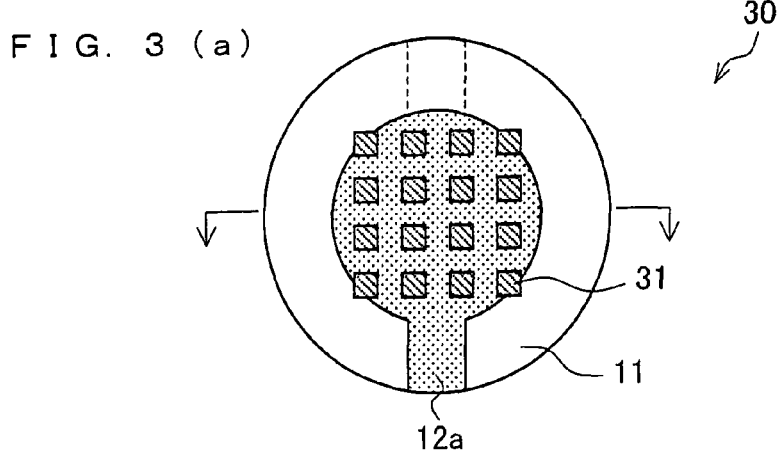
FIG. 3(a) is a top view illustrating a structure of a detector according to one embodiment, viewed from above.
FIG. 3(b) is a cross sectional view of the detector illustrated in FIG. 3(a).
Figure 3:
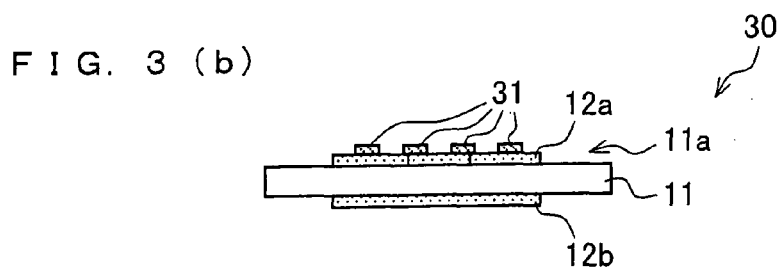

FIG. 3(a) is a top view illustrating a structure of a detector according to one embodiment, viewed from above. FIG. 3(b) is a cross sectional view of the detector illustrated in FIG. 3(a). As illustrated in FIGS. 3(a) and 3(b), a detector 30 according to the present embodiment includes an adsorption layer 31, a crystal plate 11, and metal electrodes 12a and 12b. The crystal plate 11, and the metal electrodes 12a and 12b are similar to the corresponding ones in Embodiment 1, meanwhile the adsorption layer 31 is provided on plural parts of the surface of the metal electrode 12a.

That is, the detector 30 has the same arrangement as a conventional detector (such as the detector 100 as illustrated in FIGS. 7(a) and 7(b)), except that fine segmentations of the adsorption layer 31 are provided respectively on plural parts of that surface of the metal electrode which will contact with the measurement-target substance.

For example, the detector 30 can be easily produced by etching away parts of the adsorption layer 1 of the detector 10 of Embodiment 1.

In this arrangement, the adsorption layer 31, which is coated with hydroxyapatite or the like, is provided on part or parts of the surface of the detector 30. This arrangement makes it possible to easily adjust the adsorption layer 30 as desired in terms of total adsorption area (surface area) that largely influences adsorption property of the adsorption layer 30. Thereby, it becomes possible to control detection sensitivity. Moreover, a kind of the substance that the adsorption layer 31 adsorbs or a absorption direction in which the adsorption layer 31 adsorbs can be controlled by appropriately adjusting a dimension and/or shape of the adsorption layer 31 according to which kind of substance is to be measured. Therefore, the detector 30 according to the present embodiment makes it possible to control adsorption selectivity, adsorption direction, and adsorption efficient for the measurement-target substance. This arrangement is applicable to analysis on adsorption mechanism.

[Embodiment 4]

One embodiment of the present invention is described below, referring to FIGS. 4(a) and 4(b). Note that the same constituent elements having the same function as the corresponding ones in Embodiments 1 to 3 are labeled in the same manner and their explanation is omitted here. That is, only the difference from Embodiments 1 to 3 is described here.

Figure 4:
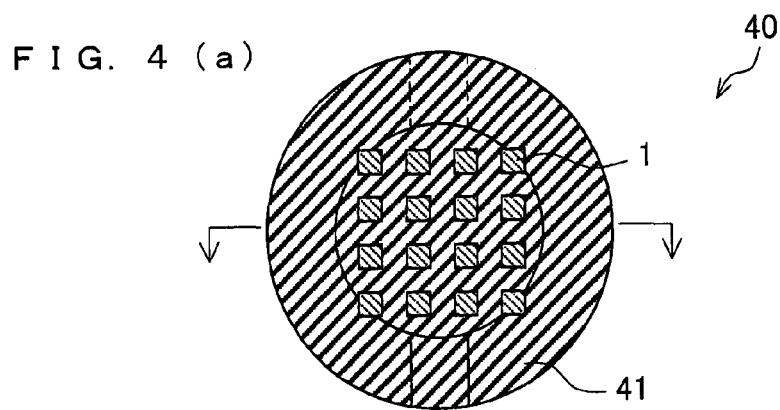
FIG. 4(a) is a top view illustrating a structure of a detector according to one embodiment, viewed from above.
FIG. 4(b) is a cross sectional view of the detector illustrated in FIG. 4(a).
Figure 4:
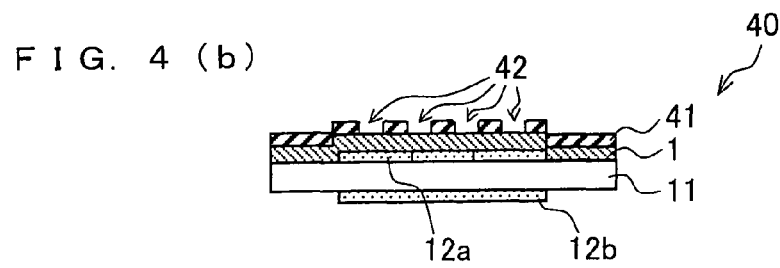

FIG. 4(a) is a top view illustrating a structure of a detector according to one embodiment, viewed from above. FIG. 4(b) is a cross sectional view of the detector illustrated in FIG. 4(a). As illustrated in FIGS. 4(a) and 4(b), a detector 40 according to the present embodiment includes an adsorption layer 1, a crystal plate 11, metal electrodes 12a and 12b, and a non-adsorption layer 41. The non-adsorption layer 41 is made of a material that does not adsorb a measurement-target substance in a sample (medium). For example, a material such as silicone resin, polytetrafluoro ethylene or the like is preferable to form the non-adsorption layer 41. However, the present invention is not limited to these.

The adsorption layer 1, crystal plate 11, and metal electrodes 12a and 12b are arranged similar to the corresponding ones in Embodiment 1. The adsorption layer 1 is formed all over that surface 11a of the crystal plate 11 which includes the metal electrode 12a. The non-adsorption layer 41 covers a surface of the adsorption layer 1. The non-adsorption layer 41 has opening sections 42 for allowing the adsorption layer 1 to contact with a measurement-target substance in a sample (medium).

That is, the detector 40 adsorbs the measurement-target substance at that parts of the adsorption layer 1 which are exposed through the opening sections 42 formed in fine size. With the arrangement in which the non-adsorption layer 41 and the opening section 42 are formed such that the openings 42 are formed on part or parts of the detector 40, it becomes possible to easily adjust the adsorption layer 1 as desired in terms of total adsorption area (surface area) that largely influences adsorption property of the adsorption layer 1. Thereby, it becomes possible to control detection sensitivity. Moreover, a kind of the substance that the adsorption layer 1 adsorbs or a absorption direction in which the adsorption layer 1 adsorbs can be controlled by appropriately adjusting a dimension and/or shape of the adsorption layer 1 according to which kind of substance is to be measured. Therefore, like Embodiment 3, the detector 40 according to the present embodiment makes it possible to control adsorption selectivity, adsorption direction, and adsorption efficient for the measurement-target substance. This arrangement is applicable to analysis on adsorption mechanism.

For example, the detector 40 can be easily produced by etching away parts of the non-adsorption layer 41.

[Embodiment 5]

One embodiment of the present invention is described below, referring to FIGS. 5(a) and 5(b). Note that the same constituent elements having the same function as the corresponding ones in Embodiments 1 to 4 are labeled in the same manner and their explanation is omitted here. That is, only the difference from Embodiments 1 to 4 is described here.

Figure 5:
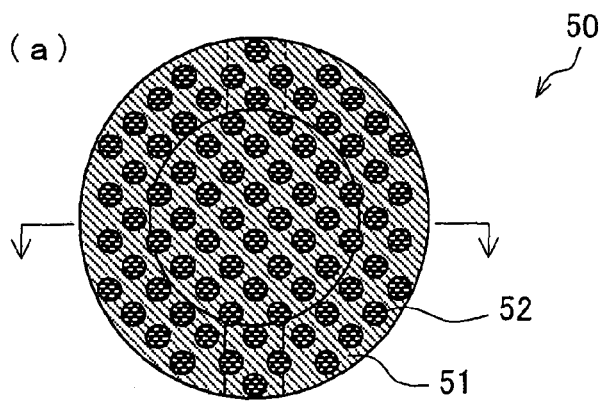
FIG. 5(a) is a top view illustrating a structure of a detector according to one embodiment, viewed from above.
FIG. 5(b) is a cross sectional view of the detector illustrated in FIG. 5(a).
Figure 5:
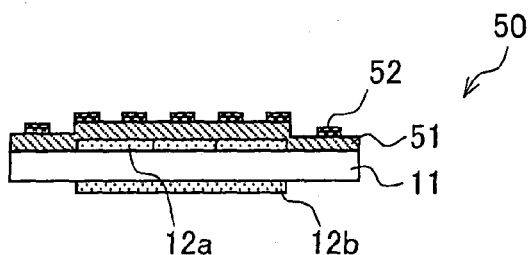
Figure 6:
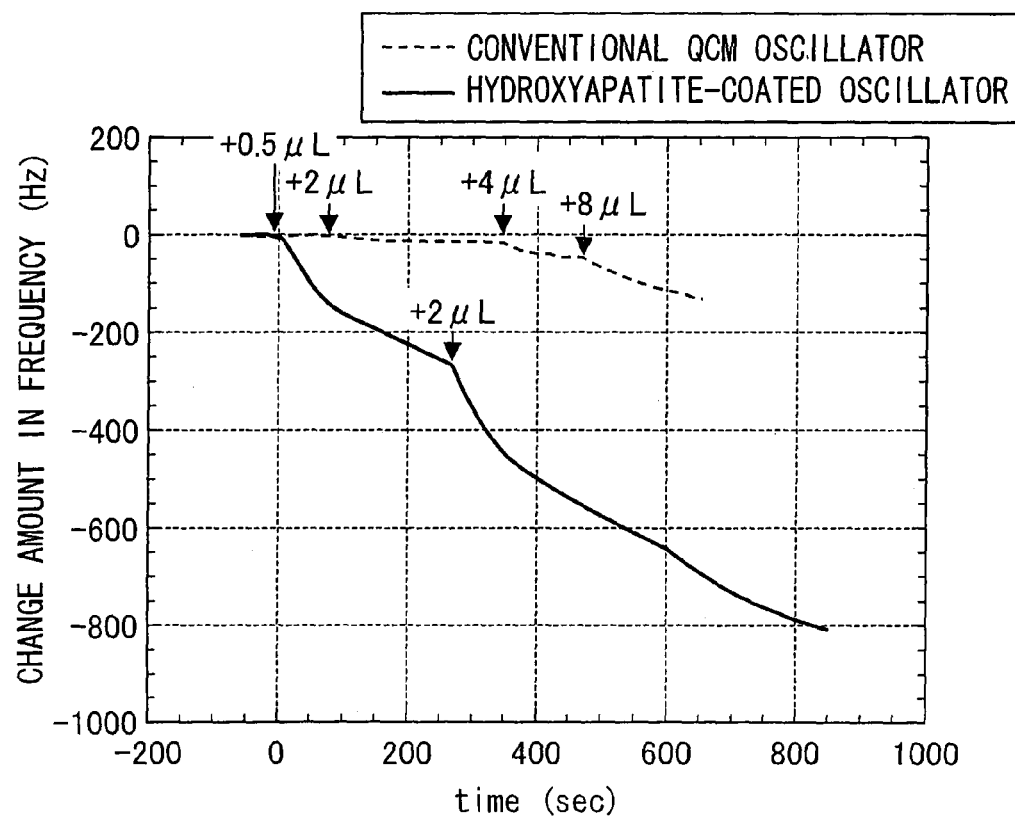
FIG. 6 is a view illustrating results of detection sensitivity test of a detector in Example.

FIG. 5(a) is a top view illustrating a structure of a detector according to one embodiment, viewed from above. FIG. 5(b) is a cross sectional view of the detector illustrated in FIG. 5(a). As illustrated in FIGS. 5(a) and 5(b), a detector 50 according to the present embodiment includes an adsorption layer 51, a crystal plate 11, and metal electrodes 12a and 12b. The crystal plate 11, and metal electrodes 12a and 12b are arranged similar to the corresponding ones in Embodiment 1. The adsorption layer 51 is formed all over that surface 11a of the crystal plate 11, which includes the metal electrode 12a.

The adsorption layer 51 contains a specifically-bonding substance 52, as well as hydroxyapatite or element-substituted apatite. That is, the specifically-bonding substance 52 causes the adsorption layer 51 to be selective to the measurement-target substance.

Coating to form the adsorption layer 51 may be carried out with a material in which specifically-bonding substance 52 is already added. In some cases, however, the adsorption layer 51 formed by coating may be heat-treated in order to attain higher crystallinity. Thus, it is preferable to apply the specifically-bonding substance 52 on the surface of the adsorption layer 51 after the heat treatment.

In this arrangement, the detector 50 includes the adsorption layer 51 containing the specifically-bonding substance 52 (for example, a ligand, antibody, inducing-factor for particular cells, or the like). Thus, the adsorption layer 51 is selective to the measurement-target substance and adjusted as to bonding strength with the measurement-target substance.

<2. Use of Detector>

As described above, the detector according to the present invention includes an adsorption layer that contains a substance (such as hydroxyapatite or the like) that shows excellent adsorption, as described above. The use of the detector according to the present invention in a chemical sensor apparatus makes it possible to detect a chemical substance in a minute quantity with high sensitivity.

Thus, the present invention encompasses such a chemical sensor apparatus including the detector. The chemical sensor apparatus according to the present invention is not particularly limited, provided that it includes the detector. Any chemical sensor apparatus to which the detector can be employed can be adopted as the chemical sensor apparatus. Especially, chemical sensor apparatuses using QCM method or SPR method are preferable.

As described above, the detector according to the present invention or a chemical sensor apparatus according to the present invention including the detector makes it possible to perform (i) highly sensitive detection of a chemical substance (such as a biomolecule, a ligand, a protein, an antibody, an inducing-factor for particular cells, environmental substance, or the like) that a medium such as liquid, gas, or the like contains as its content or particles contained therein, or (ii) highly sensitive detection of interaction between particles (between protein and protein, between antibody and antigen, between hormone and receptor, between protein and nucleic acid, between substrate and enzyme, between DNA complementary pairs, etc.) in the medium. Further, the high detection sensitivity for a chemical substance in a minute substance allows wider measurable ranges for gene, antigen substance, smell, taste, environmental substance (environmental hormone) etc.

The present invention encompass methods for detecting a contaminant or content in a medium or interaction between particles by using a chemical sensor apparatus (such as apparatus using the quartz crystal method (QCM method), a surface plasmon resonance sensor, or the like apparatus) for detecting a substance in a minute quantity, the apparatus having a detector section having a surface coated with hydroxyapatite or an element-substituted apatite (a hydroxyapatite, part of whose elements is substituted) Furthermore, the present invention encompasses detectors for use in chemical sensor apparatus, the detectors having an electrode(s) made of an element-substituted apatite that is electrically conductive. Moreover, the present invention encompasses detectors for use in chemical sensor apparatus, the detectors having an adsorption layer made of an element-substituted apatite that is biocompatible.

Furthermore, the present invention encompasses a chemical sensor apparatus including a detector having a surface which is coated with a hydroxyapatite coating film. Further, the present invention encompasses a chemical sensor apparatus in which plural parts of a surface of a detector is coated with a hydroxyapatite coating film. Moreover, the present invention encompasses a detector for use in a chemical sensor apparatus, the detector having been etched to attain the oscillator as described above, or having an adsorption layer being partly coated with another material so as to attain the oscillator as described above. Furthermore, the present invention encompasses a detector for use in a chemical sensor apparatus in which an intermediate material have been added in advance to any one of the adsorption layers in order to adjust a bonding force between the material to be detected and the oscillator.

The embodiments of the present inventions are described in more details via Examples described below. Needless to say, the present invention is not limited to the following Examples, and may be modified in various ways in details. Furthermore, the present invention is not limited to the embodiment described above. The present invention can be modified in various ways within the scope of the following claims. The technical scope of the present invention covers embodiments obtained by appropriately combining the technical means disclosed herein.

EXAMPLES

A QCM detector coated with a hydroxyapatite was prepared in the following manner. It was tested whether or not the user of the detector improved the QCM method in detection sensitivity for detecting a substance to be detected.

By the laser ablation method, hydroxyapatite was deposited to 100 nm thickness on a commercially-available QCM detector (AFFINIXO sensor chip, made by Initium Inc.). Then, the detector was heat-treated so as to attain higher crystallinity. Thereby, hydroxyapatite-coated QCM detector was obtained. As a detector (sensor), the hydroxyapatite-coated QCM detector was attached to a QCM chemical sensor apparatus (AFFINIXO, made by Initium Inc.). This QCM chemical sensor apparatus and a chemical sensor apparatus with a conventional sensor were compared in sensitivity in detection of a bovine-derived blood serum dropped in 8 mL (eight milliliters) of a physiological buffer saline (PBS) solution.

The chemical sensor apparatus with the conventional sensor showed frequency shifts as indicated by the dotted line in FIG. 7 for samples in which 0.5, 2, 4, and 8 μL (microliters) of the blood serum was dropped respectively. On the other hand, the chemical sensor apparatus with the hydroxyapatite-coated QCM detector showed frequency shifts as indicated by the solid line for samples in which 0.5 and 2 μL of the blood serum was dropped respectively. This confirmed that the detection sensitivity was significantly improved in the chemical sensor apparatus with the hydroxyapatite-coated QCM detector.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Industrial Applicability

As described above, according to a detector according to the present invention and a chemical sensor apparatus according to the present invention using the detector, it is possible to improve a detection sensitivity significantly, compared with conventional detectors and chemical sensor apparatuses. The detector according to the present invention and the chemical sensor apparatus according to the present invention make it possible to detect chemical substances in minute quantities that have been undetectable. Therefore, the present invention is applicable to wide varieties of industries, typically industries related to chemicals, medicines, foods, etc.

The invention claimed is:

1. A detector for use in a chemical sensor apparatus, the detector detecting a measurement-target substance in a medium by detecting adsorption of the measurement-target substance on a detection surface of the detector, the detector comprising:
(i) an adsorption layer on the detection surface for detecting the substance, the adsorption layer including an element-substituted apatite,
(ii) a crystal plate or a substrate,
(iii) a metal electrode,
the chemical sensor apparatus employing a quartz crystal microbalance method or a surface plasmon resonance method,
wherein the element-substituted apatite is a hydroxyapatite including both Ca and a phosphate group, part of whose elements is substituted with Na,
wherein the adsorption layer and the metal electrode are provided on opposing sides of the crystal plate or the substrate, such that the adsorption layer and the metal electrode face each other with the crystal plate or the substrate disposed between the adsorption layer and the metal electrode.

2. The detector as set forth in claim 1, wherein the adsorption layer is provided over the whole detection surface.

3. The detector as set forth in claim 1, wherein the adsorption layer is provided over plural parts of the detection surface.

4. The detector as set forth in claim 1, wherein the adsorption layer includes an element-substituted apatite that is biocompatible.

5. The detector as set forth in claim 1, including:
a non-adsorption layer on a surface of the adsorption layer, the non-adsorption layer having an opening for allowing the adsorption layer to contact with the substance in the medium.

6. The detector as set forth in any claim 1, wherein the adsorption layer further includes a substance for bonding specifically to the measurement-target substance so that the adsorption layer selectively adsorbs the measurement-target substance.

7. The detector as set forth in claim 1, wherein the adsorption layer is formed by a laser ablation method.

8. The detector as set forth in claim 1, wherein the adsorption layer is improved in crystallinity of the element-substituted apatite by being subjected to heat treatment or sintering treatment during or after formation of the adsorption layer.

9. A detector for use in a chemical sensor apparatus, the detector detecting a measurement-target substance, which is contained in a medium and adsorbed on a detection surface of the detector, the detector comprising:
(i) an adsorption layer on the detection surface for detecting the substance, the adsorption layer including hydroxyapatite, the hydroxyapatite including both Ca and a phosphate group, wherein the hydroxyapatite has constituent elements substituted with Na,
(ii) a crystal plate or a substrate,
(iii) a metal electrode,
the adsorption layer being formed by a laser ablation method,
wherein the adsorption layer and the metal electrode are provided on opposing sides of the crystal plate or the substrate, such that the adsorption layer and the metal electrode face each other with the crystal plate or the substrate disposed between the adsorption layer and the metal electrode.

10. The detector as set forth in claim 9, wherein the adsorption layer is improved in crystallinity of hydroxyapatite by being subjected to heat treatment or sintering treatment during or after formation of the adsorption layer.

* * * * *